US006868851B2

(12) United States Patent
Heinonen

(10) Patent No.: US 6,868,851 B2
(45) Date of Patent: Mar. 22, 2005

(54) LIQUID RESERVOIR FOR NEBULIZER

(75) Inventor: Erkki Heinonen, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 39 days.

(21) Appl. No.: 10/062,176

(22) Filed: Jan. 31, 2002

(65) Prior Publication Data

US 2003/0140919 A1 Jul. 31, 2003

(51) Int. Cl.[7] .............................................. A61M 11/00
(52) U.S. Cl. ............................. 128/200.22; 128/203.12
(58) Field of Search ....................... 128/203.12, 200.22, 128/200.21, 200.14; 222/321.1, 321.8, 383.1, 384; 239/321, 518, 524, 543, 544, 79–85, 102.2, 327, 330, 331, 338

(56) References Cited

U.S. PATENT DOCUMENTS

| | | | | | |
|---|---|---|---|---|---|
| 293,730 | A | * | 2/1884 | Goldman | 239/327 |
| 320,346 | A | * | 6/1885 | Goldman | 222/207 |
| 594,520 | A | * | 11/1897 | Bunnell et al. | 222/210 |
| 644,703 | A | * | 3/1900 | Buckley | 239/327 |
| 671,423 | A | * | 4/1901 | McTernen | 239/327 |
| 725,954 | A | * | 4/1903 | Goldman | 239/327 |
| 798,093 | A | * | 8/1905 | Dean | 604/204 |
| 1,754,382 | A | * | 4/1930 | Baracate | 228/53 |
| 2,578,864 | A | * | 12/1951 | Tupper | 222/215 |
| 2,625,432 | A | * | 1/1953 | Tupper | 239/327 |
| 2,760,209 | A | * | 8/1956 | Ewing et al. | 4/223 |
| 2,766,907 | A | * | 10/1956 | Wallace, Jr. | 222/94 |
| 2,870,574 | A | * | 1/1959 | Sheridan | 47/62 E |
| 3,089,624 | A | * | 5/1963 | Micallef | 222/386.5 |
| 3,259,321 | A | * | 7/1966 | Sellers | 239/310 |
| 3,404,843 | A | * | 10/1968 | Szekely | 239/338 |
| 3,848,808 | A | * | 11/1974 | Fetty et al. | 239/327 |
| 4,047,642 | A | * | 9/1977 | Nilson | 222/94 |
| 4,191,181 | A | * | 3/1980 | Franetzki et al. | 604/151 |
| 4,224,940 | A | | 9/1980 | Monnier | |
| 5,221,050 | A | * | 6/1993 | Jeffries et al. | 239/708 |
| 5,487,378 | A | * | 1/1996 | Robertson et al. | 128/200.16 |
| 5,497,944 | A | * | 3/1996 | Weston et al. | 239/321 |
| 5,515,842 | A | * | 5/1996 | Ramseyer et al. | 128/200.18 |
| 5,662,271 | A | * | 9/1997 | Weston et al. | 239/321 |
| 5,823,179 | A | * | 10/1998 | Grychowski et al. | 128/200.18 |
| 5,894,841 | A | | 4/1999 | Voges | |
| 5,957,891 | A | * | 9/1999 | Kriesel et al. | 604/132 |
| 6,029,660 | A | * | 2/2000 | Calluaud et al. | 128/203.12 |
| 6,056,213 | A | | 5/2000 | Ruta et al. | |
| 6,659,364 | B1 | * | 12/2003 | Humberstone et al. | 239/4 |

FOREIGN PATENT DOCUMENTS

| | | |
|---|---|---|
| EP | 1219313 | 7/2002 |
| EP | 1219314 | 7/2002 |
| WO | 01/19437 | 3/2001 |

* cited by examiner

*Primary Examiner*—Aaron J. Lewis
(74) *Attorney, Agent, or Firm*—Andrus, Sceales, Starke & Sawall, LLP

(57) ABSTRACT

A liquid reservoir for a nebulizer is comprised of a pair of membranes formed of resilient material and sealed about their edges to form a closed chamber between them for containing a liquid to be nebulized. When the chamber is filled with liquid and thereby expanded, the resilient membranes are distended to apply pressure to the liquid in the chamber. A discharge valve controls the discharge of liquid from the reservoir to the nebulizer under the pressure applied by the membranes. The reservoir is mounted on the nebulizer so that one of the membranes abuts a surface of the nebulizer that concavely deforms the membrane to increase the pressure applied to the liquid in the chamber to reduce or eliminate any residual volume of liquid in the chamber at the end of the discharging operation.

20 Claims, 4 Drawing Sheets

LIQUID RESERVOIR FOR NEBULIZER

BACKGROUND OF THE INVENTION

The present invention relates to nebulizers and more particularly to an improved reservoir arrangement for containing a liquid to be nebulized.

Nebulizers, or atomizers, are devices that generate a fine spray or aerosol. A particularly useful application for nebulizers is to convert aqueous drug solutions, or suspensions with non-dissolved particles, into an aerosol of small droplets that can thereafter be inhaled to administer the drug to a subject during breathing. Such inhalation treatment is highly effective for conditions effecting the subject's respiratory organs. Further, since the lungs are close to the heart and the blood circulatory system of the body, drug administration by inhalation provides an effective and rapid delivery system to all organs of the body.

In many cases, the subject breathes with the aid of a respiratory ventilator. A typical ventilator has a breathing circuit comprising an inhalation limb and an exhalation limb connected to two arms of a Y-connector. The third arm of the Y-connector is connected via a patient limb to a mouth piece, mask, or endotracheal tube for the subject. The ventilator provides a desired degree of assistance to the breathing of the subject during the inhalation phase of the respiratory cycle. The contraction of the subject's lungs discharges gas through the exhalation limb during exhalation. To achieve the maximum physiological effect for the subject and to avoid wastage of the drug, the nebulizing action of the nebulizer is synchronized with the inspiratory phase of the respiratory cycle. A typical example of a nebulizer arrangement is shown in U.S. patent application Ser. No. 09/397,529, filed Sep. 16, 1999; Ser. No. 09/547,523, filed Apr. 12, 2000; and Ser. No. 09/699,049, filed Oct. 30, 2000 and European Patent Applications 311,773.6, filed Dec. 29, 2000 and 311,778.5, filed Dec. 29, 2000 which applications are incorporated herein by reference to the extent permitted. In nebulizers of the type shown in the foregoing U.S. and European patent applications, the liquid is converted to an aerosol by the action of a vibrating element, such as a piezoelectric element. The supply of liquid from a liquid reservoir to the nebulizing element is controlled by a valve. The liquid reservoir is pressurized to cause the liquid to flow through the valve to the element when the valve is open.

In order to ensure maximum penetration depth of a nebulized drug into the lungs of the subject, the gas volume in the breathing circuit between the nebulizer and the lung should be minimized. To this end, the nebulizer is typically positioned near the patient mouth piece, mask, or endotracheal tube, i.e., in the patient limb of the breathing circuit described above. However, for surgical and intensive care patients, the area around the nose, mouth, neck and upper chest is often critical to the care of the patient and/or crowded with other equipment. The overall size of the nebulizer, including its liquid reservoir, thus becomes very important. A liquid container remote from the nebulizer may be used to reduce the size of the nebulizer. However, if a small volume of drug is to be delivered, such an arrangement can be disadvantageous because of the amount of drug required to fill the liquid supply line between the container and the nebulizer and the residuum of drug left in the supply line. A local liquid reservoir mounted on the nebulizer would thus be advantageous in such circumstances.

Such a local liquid reservoir for a nebulizer typically comprises two compartments separated by a moving wall.

One compartment contains the liquid drug. The other compartment contains a pressurizing gas. The moving wall ensures that the drug is not contaminated by the gas. The liquid compartment is filled with the drug by a syringe through a filling port. A syringe may also be used to pressurize the gas compartment. The reservoir so filled is mounted on the nebulizer to supply liquid to the vibrating element of the nebulizer.

However, in such a local liquid reservoir, the gas compartment adds to the overall size of the reservoir. As noted above, size is a serious concern for certain uses of the nebulizer. Also, pressurization of the gas compartment is an additional maneuver required when using a nebulizer of this type.

Another requirement for a local reservoir for a nebulizer is that it be able to generate the necessary pressure to deliver liquid from the liquid compartment to the nebulizing element, including cases in which the inhalation limb and patient limb are pressurized by the ventilator to provide breathing gases to the subject. It is also desirable that the liquid reservoir be capable of supplying the liquid independently of the position or orientation of the nebulizer. To ensure that a proper drug dosage is administered to the subject and to avoid wastage of drug, it is desirable that the reservoir be capable of being completely emptied. It should be easy to fill the reservoir. At the end of the drug administration, the reservoir should be easy to clean or dispose of. And, as noted above, the reservoir should be as small as possible, commensurate with the volume of liquid to be delivered to the subject.

BRIEF SUMMARY OF THE INVENTION

It is the object of the present invention to provide an improved local liquid reservoir means for a nebulizer that advantageously meets the foregoing and other requirements.

Briefly, the present invention contemplates such a liquid reservoir comprised of a pair of membranes formed of a resilient material. The membranes are positioned in an opposing relationship and sealed about their edges to form a closed chamber between them for containing the liquid to be nebulized. The chamber may be filled by a syringe or other appropriate means. Or, the chamber may be filled directly from a container through a check valve using a handle or other means, to draw the membranes apart in which case, the use of a syringe may be eliminated. When the chamber is filled with liquid and thereby expanded, the expansion of the chamber distends the resilient material membranes to apply pressure to liquid in the chamber. A flow control means, such as a valve, communicates with the chamber and controls the discharge of liquid from the reservoir to the nebulizer under the pressure applied to the liquid by the distended membranes.

The liquid reservoir is mounted on the nebulizer so that one of the membranes abuts a surface of the nebulizer which concavely deforms the membrane to increase the pressure applied to the liquid in the chamber. This pressure increase ensures that the liquid can be discharged from the chamber against any pressures generated in a breathing circuit to which the nebulizer is connected. It further renders the nebulizer insensitive to position as gases from the breathing circuit cannot enter and become trapped in the reservoir. Still further, it reduces or eliminates any residual volume of liquid in the chamber at the end of treatment, thereby ensuring that a patient receives the proper total dosage of a drug and avoiding wastage.

Inasmuch as the local liquid reservoir of the present invention does not use a pressurizing gas, the overall size of the reservoir can be advantageously reduced due to the absence of a gas chamber.

The invention will be further understood from the following detailed description, taken in conjunction with the drawing.

DETAILED DESCRIPTION OF THE PREFERRED EMBODIMENTS

Figure 1:
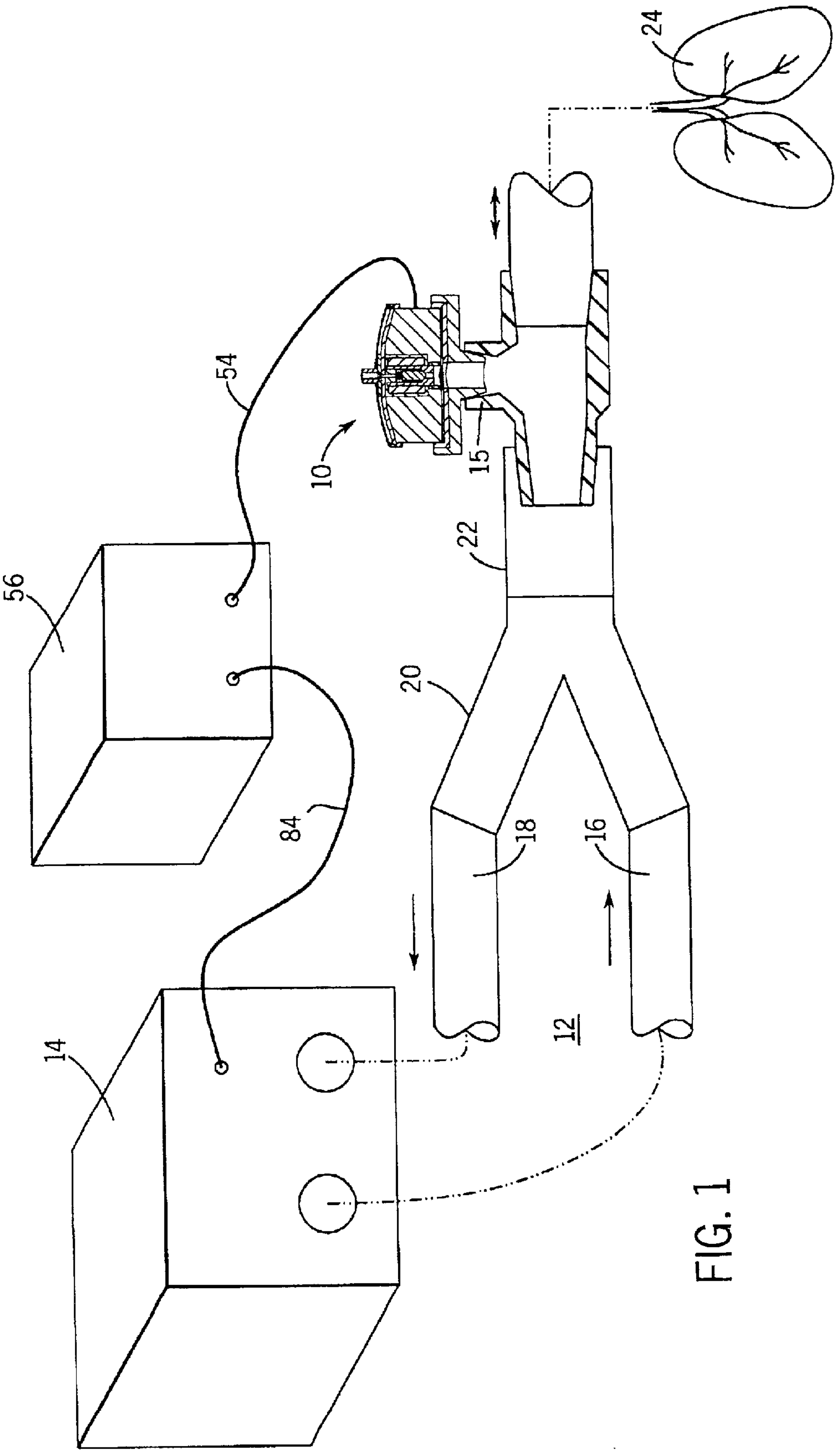
FIG. 1 is a general schematic view of ventilator apparatus containing a nebulizer with a liquid reservoir means according to the present invention.

Nebulizer apparatus 10 of the present invention is typically used in conjunction with breathing circuit 12 and ventilator 14, as shown in FIG. 1. Nebulizer 10 atomizes liquid solutions or suspensions for delivery to a subject, as for example as a drug treatment for a patient. Breathing circuit 12 includes inhalation limb 16 coupled to ventilator 14. Exhalation limb 18 is also connected to ventilator 14. Inhalation limb 16 and exhalation limb 18 are connected to two arms of Y-connector 20. The third arm of Y-connector 20 is connected to one end of patient limb 22. The other end of patient limb 22 is connected to a mouthpiece, face mask, or endotracheal tube (not shown) for the subject for supplying respiratory gases to lungs 24 of a subject.

Ventilator 14 provides all or a portion of the respiratory gases for the subject by providing inhalation gases in inhalation limb 16. The inhalation gases pass through Y-connector 20 and into patient limb 22 for supply to the lungs 24 of the subject. On exhalation, the respiratory gases pass through patient limb 22, Y-connector 20, and exhalation limb 18 back to ventilator 14.

As shown in FIG. 1, nebulizer apparatus 10 is preferably positioned in patient breathing circuit 12 as near the subject as possible to ensure effective delivery of the atomized liquid to lungs 24 of the subject and to minimize the deposition of the liquid on the breathing circuit walls. To this end, nebulizer apparatus 10 may be inserted in the breathing circuit between Y-connector 20 and patient limb 22 as shown in FIG. 1.

Figure 2:
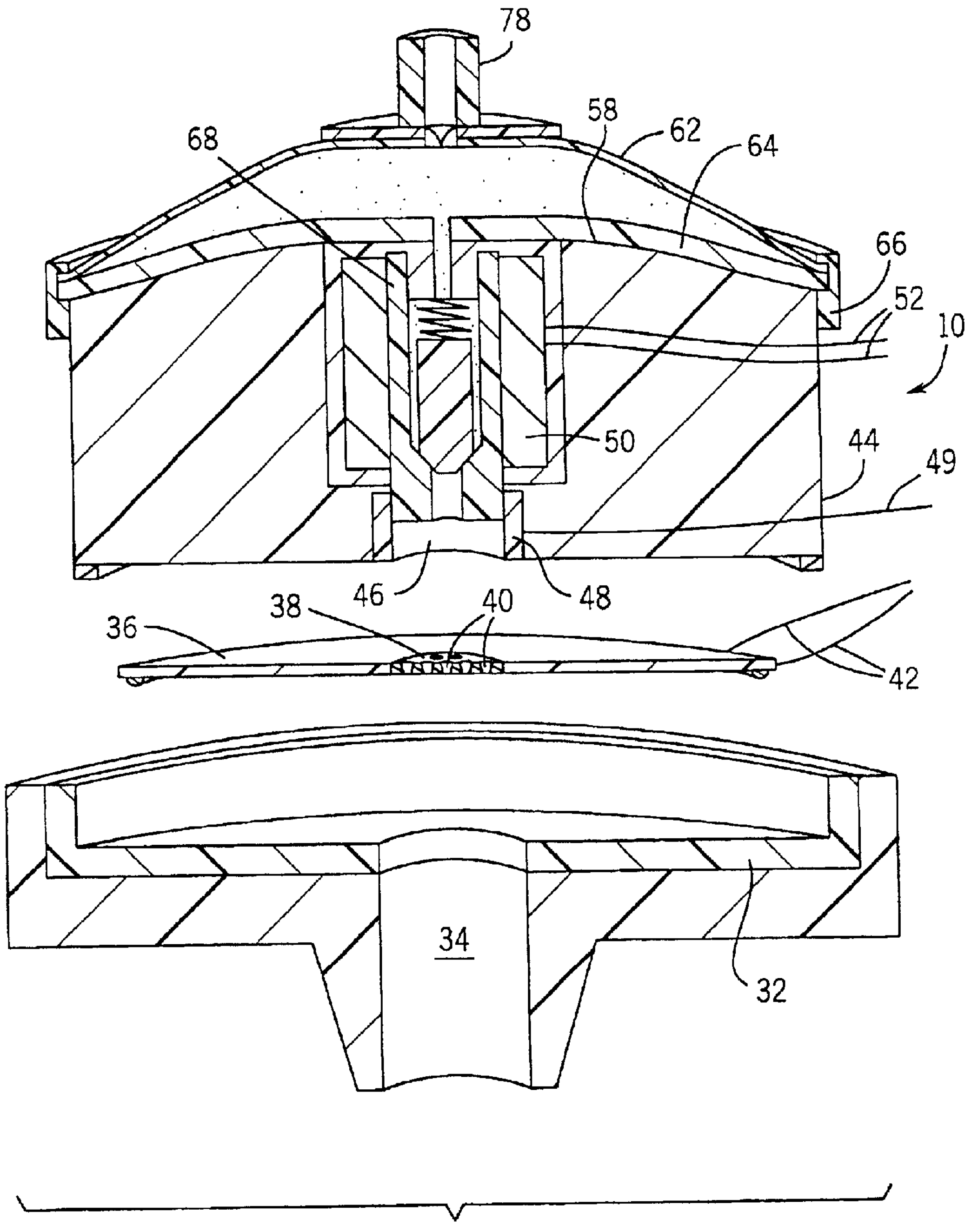
FIG. 2 is a general exploded and schematic cross sectional view of a nebulizer and liquid reservoir means of the present invention.

The construction of a nebulizer apparatus suitable for use with the liquid reservoir of the present invention is shown generally in FIG. 2. Nebulizer apparatus 10 includes adapter 30 for connecting the nebulizer apparatus in patient limb 22 of breathing circuit 12. Housing 32 is mounted in adaptor 30 in a manner to permit the housing and other portions of the nebulizer apparatus to be removed from the adaptor for cleaning, when changing drugs, or for other purposes. Housing 32 contains opening 34 through which nebulized liquid may pass.

A vibrating element 36, such as a piezoelectric element, is mounted in housing 32. The central portion of the vibrating element comprises a mesh plate 38 containing a holes 40. Holes 40 may be formed in plate 38 by an electro forming process that produces hose having a diameter of preferably approximately 2–15 $\mu$m in diameter. Vibrating element 36 may be energized by high frequency alternating voltage provided in conductors 42.

Plug member 44 is placed in the cavity defined by housing 32. Plug member 44 has a central opening 46 through which liquid to be nebulized may pass to mesh plate 38. Opening 46 may be surrounded by electrode 48 to provide, in conjunction with vibrating element 36, a capacitive means for determining the amount of liquid provided to mesh plate 38. Conductor 49 is connected to electrode 48 for this purpose. Plug member 44 also includes electromagnet 50 for operating a valve, hereinafter described. Electromagnet 50 may be energized through conductors 52. Conductors 42, 49, and 52 are contained in cable 54 connected to nebulizer control unit 56.

As shown in FIG. 2, the upper surface 58 of plug member 44 is convexly curved when viewed from the exterior of the plug member.

Figure 3:
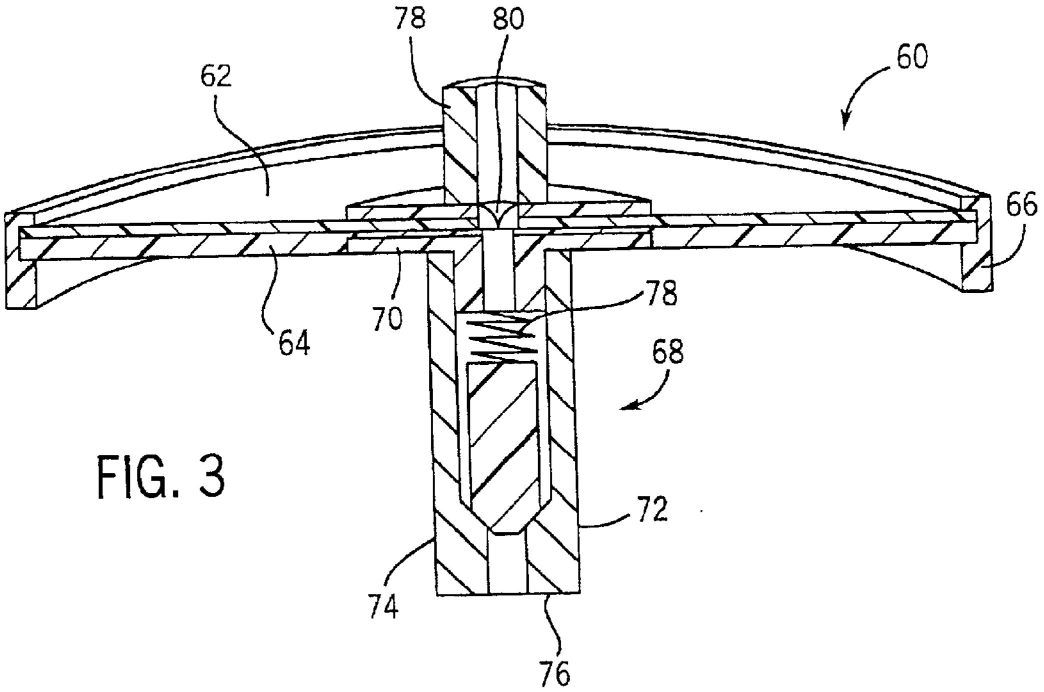
FIG. 3 shows one embodiment of the liquid reservoir of the present invention in the unfilled condition.

FIG. 3 shows one embodiment of liquid reservoir 60 of the present invention. Reservoir 60 is comprised of a first membrane 62 and a second membrane 64. As shown in FIG. 3, the membranes are juxtapositioned in a generally opposing relationship. The membranes, which are shown as circular in form in FIG. 3, are joined at their periphery and to form a closed chamber between the membranes. The peripheral edges of membranes 62 and 64 are joined to frame 66 which serves to mount reservoir 60 on plug member 44 as shown in FIG. 2. Bayonet fittings or other suitable means may be provided to fasten the reservoir on plug member 44. Membranes 62, 64 are formed of a resilient material, such as rubber or plastic.

One of the membranes, for example, membrane 64 contains a means for discharging liquid from reservoir 60. As shown in FIG. 3, the means may comprise a valve 68 which includes a disc-like plate 70 mounted in membrane 64. Liquid conveying tube 72 depends from plate 70. A stopper 74 is placed in tube 72 to rest on valve seat 76 formed in the tube. Spring 78 abuts stopper 74 to bias the stopper onto valve seat 76. As hereinafter noted, the pressure of the liquid in reservoir 60 may also be used to press stopper 74 against valve seat 76. Stopper 74 is formed of a ferromagnetic material.

Membrane 62 contains a means for filling a chamber formed between membranes 62 and 64 with liquid. As shown in FIG. 3, the means may comprise a tube or luer lock fitting 78 suitable for engaging the end of a syringe. Check valve 80 is located in tube 78 to retain the liquid in the chamber. Check valve 80 may be formed of a plastic sealing means that deforms to provide an opening through which liquid may enter the chamber formed between the membranes. Or, the filling means may have a cap for closing the filling means.

Figure 4:
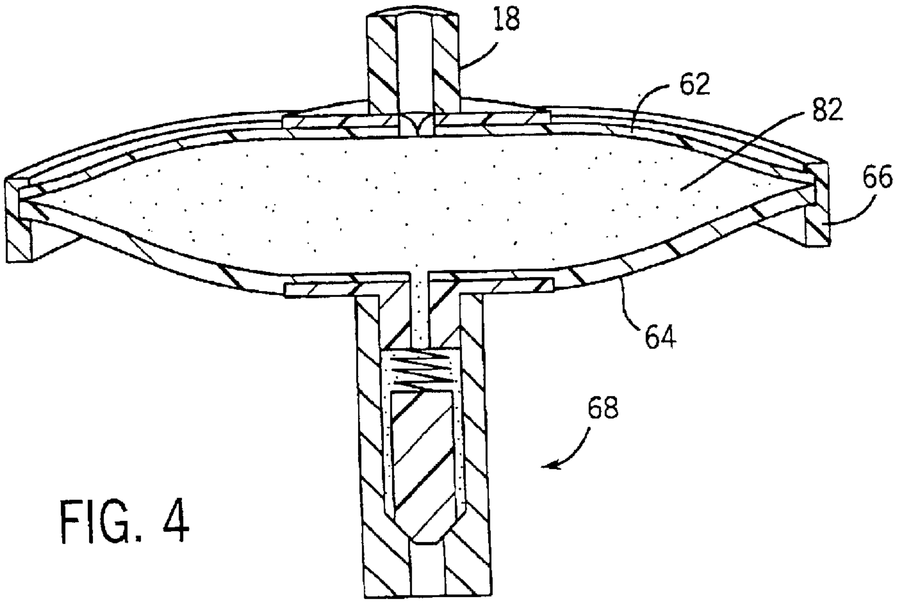
FIG. 4 is a view showing the reservoir of FIG. 3 in the filled condition.

In use, liquid reservoir 60 is filled with liquid as by connecting a syringe to tube or luer lock 78 and injecting fluid through check valve 80 between membranes 62 and 64. The injection of the fluid distends resilient membranes 62 and 64, as shown in FIG. 4, for form chamber 82. This distention pressurizes the liquid in chamber 82. The pressure in chamber 82 assists spring 78 in sealing stopper 74 on valve seat 76 to retain the liquid in chamber 82. FIG. 4 shows liquid reservoir 60 in the filled condition.

After filling, liquid reservoir 60 is placed on plug 44 to insert tube 72 through electromagnet 50 in plug 44. Membrane 64 comes into abutment with convex surface 58. As liquid reservoir 60 is pressed on surface 58, membrane 64, as well as membrane 62, is concavely deformed, as shown in FIG. 2. This further increases the pressure applied by the membranes to the liquid in chamber 82. Liquid reservoir 60 is secured to nebulizer 10 by a connection between frame 66 and plug member 44.

Electromagnet 50 is energized through conductors 52 to lift stopper 74 off valve seat 76 and allow liquid from chamber 82 to flow to mesh plate 38. Vibrating element 36 is energized through conductors 42 to nebulize the liquid and expel same through holes 40 in mesh plate 38. The energization provided in conductors 42 and 52 of cable 20 from nebulizer control unit 56 may be synchronized with the respiratory cycle of the subject so that the atomized liquid is carried into lungs 24 of the subject with the breathing gases inhaled during the inspiratory phase of the respiratory cycle. A triggering signal may be provided from ventilator 14 to nebulizer control unit 56 in conductor 84 for this purpose.

The pertinent portions of plug 44 and liquid reservoir 60 may be formed such that the pressure applied to the liquid in chamber 82 when liquid reservoir 10 is fastened to plug member 44 is sufficient to secure the removal of substantially all of the liquid from chamber 82, even against the elevated breathing circuit pressure that may be applied to chamber 82 from patient limb 22 through valve 68. That is, the pressure applied to the liquid in chamber 82 by the membranes forming the chamber can exceed the pressure in patient limb 22.

As liquid is discharged from chamber 82, membrane 62 will approach membrane 64. The convex surface of plug member 44, and the resulting concave deformation of membrane 64, is formed such that membrane 62 progressively contacts membrane 64, commencing from adjacent frame 66 and extending toward the center of the membranes. This assures that no residual liquid is left in chamber 82. For this purpose, surface 58 may be formed such that the radius of curvature increases from the edge toward the center.

The applied pressure also renders nebulizer 10 and liquid reservoir 60 insensitive to position since gas from the breathing circuit will not pass through valve 68 and become trapped in liquid reservoir 60 even if the liquid reservoir is upside down from the orientation shown in FIGS. 2 through 4.

Figure 5:
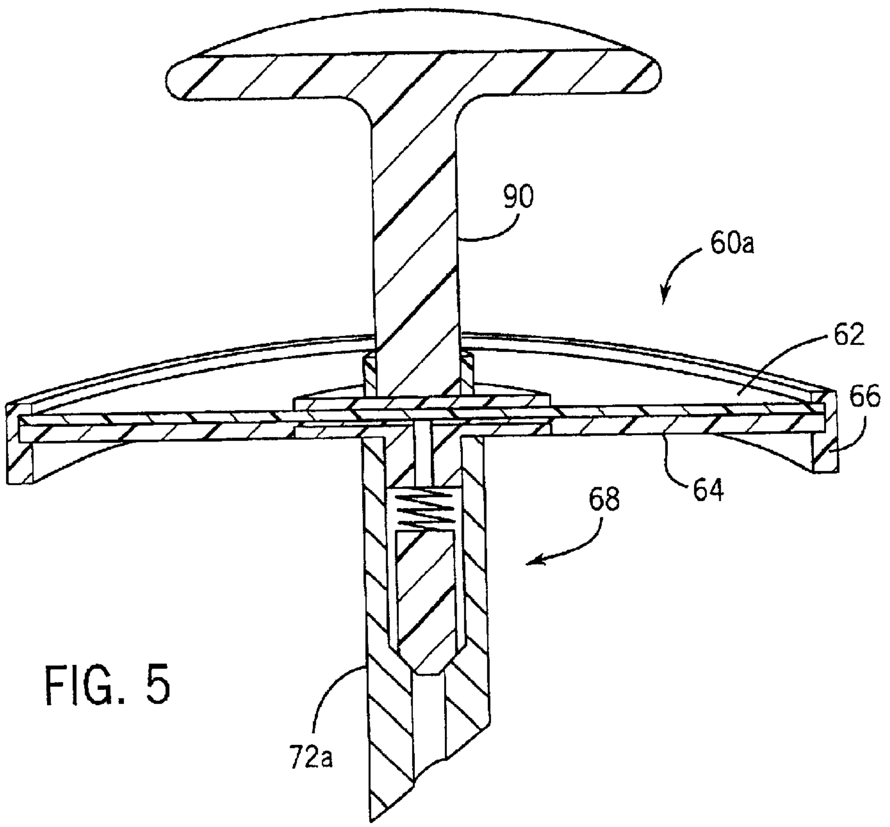
FIG. 5 shows another embodiment of the liquid reservoir of the present invention.

FIG. 5 shows a further embodiment of the liquid reservoir of the present invention. In liquid reservoir **60*a*, a handle 90 is mounted on membrane 62. The end of tube 72*a* may be sharpened, and used to penetrate a drug supply container, such as an ampoule. Handle 90 is used to separate, or pull apart, membranes 62 and 64 to create an under pressure between the membranes. This suctions the drug from the drug supply container into the chamber through valve 68 that, in this case also operates as a check valve. The need to use an intermediate device, such as a syringe, to fill chamber 82 is thus avoided although liquid reservoir 60 must be disconnected from nebulizer apparatus 10 to fill chamber 82. Handle 90 may be removable, if desired, to minimize the size of liquid reservoir 60*a***.

Figure 6:
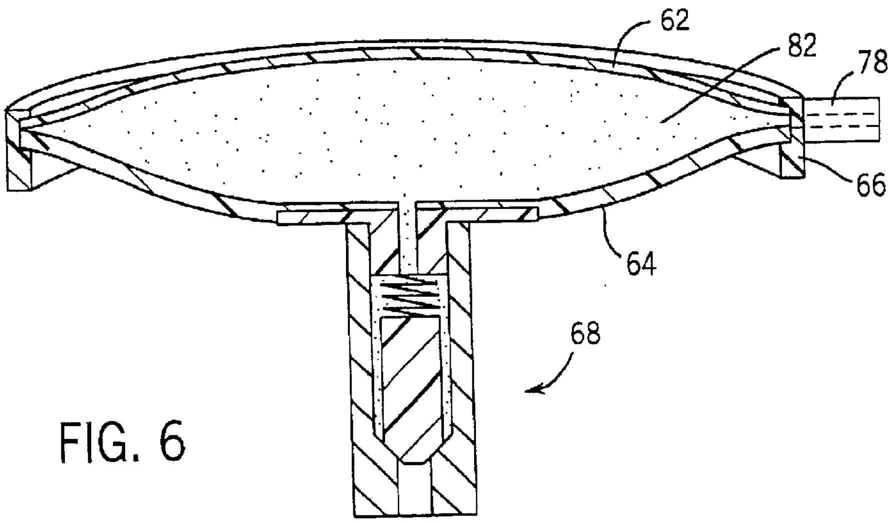
FIG. 6 shows a modification of a filling means for the liquid reservoir.
Figure 1:
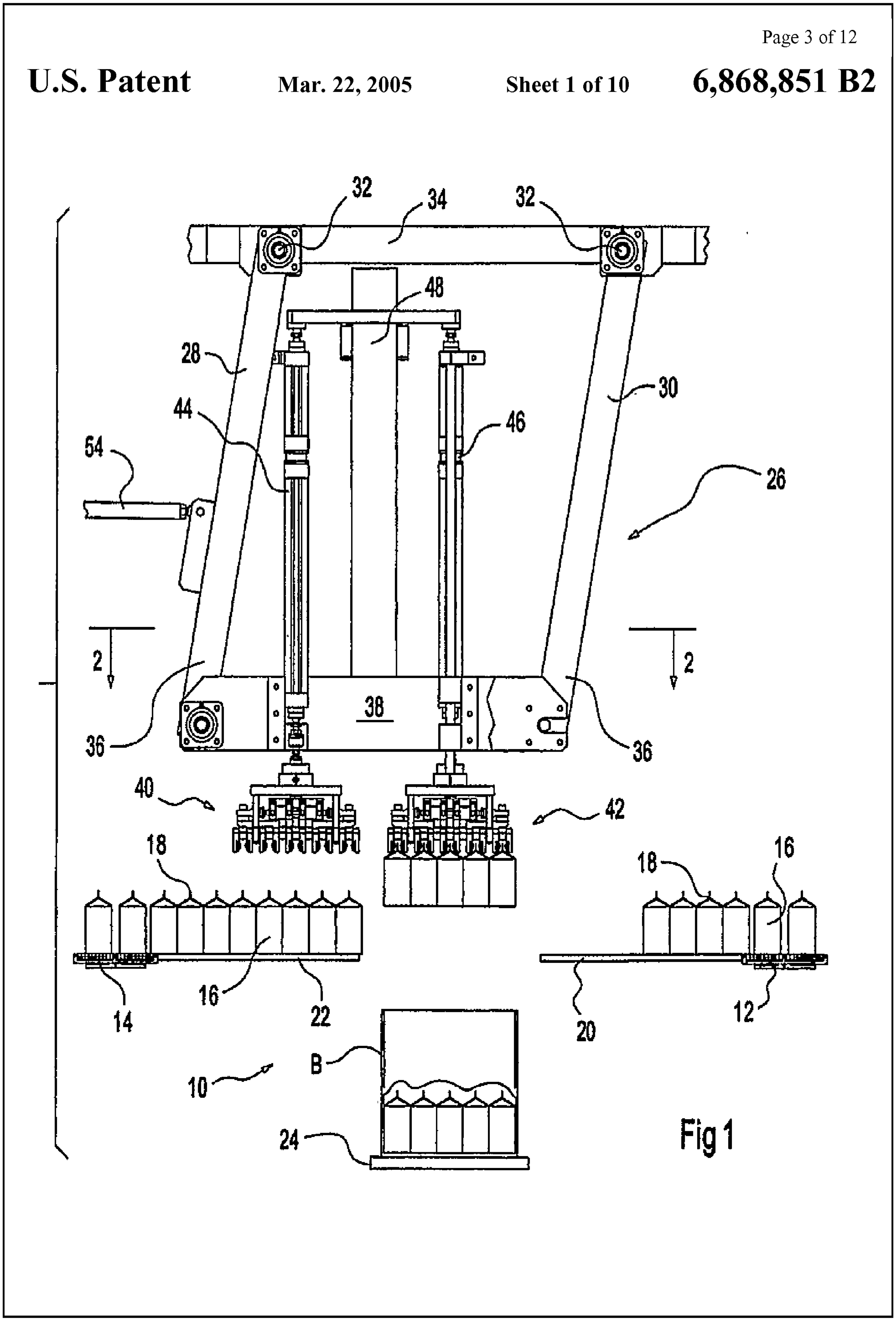
Figure 2:
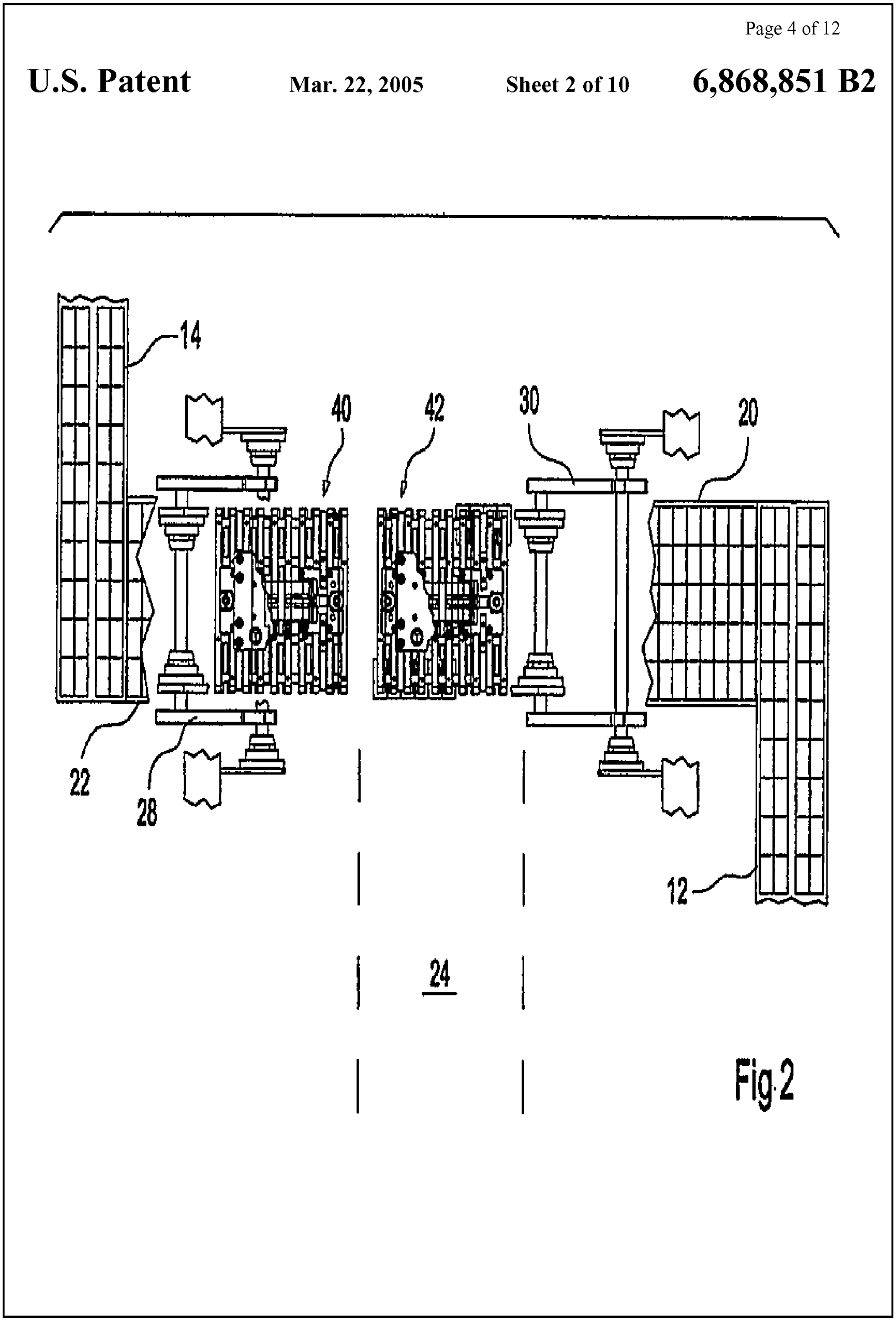
Figure 3:
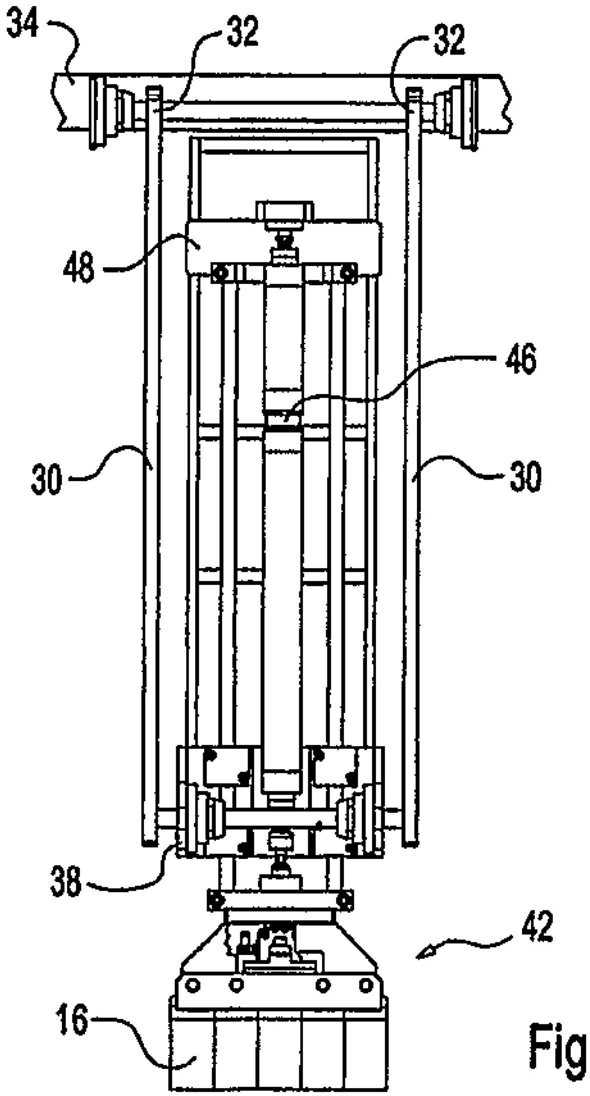
Figure 4:
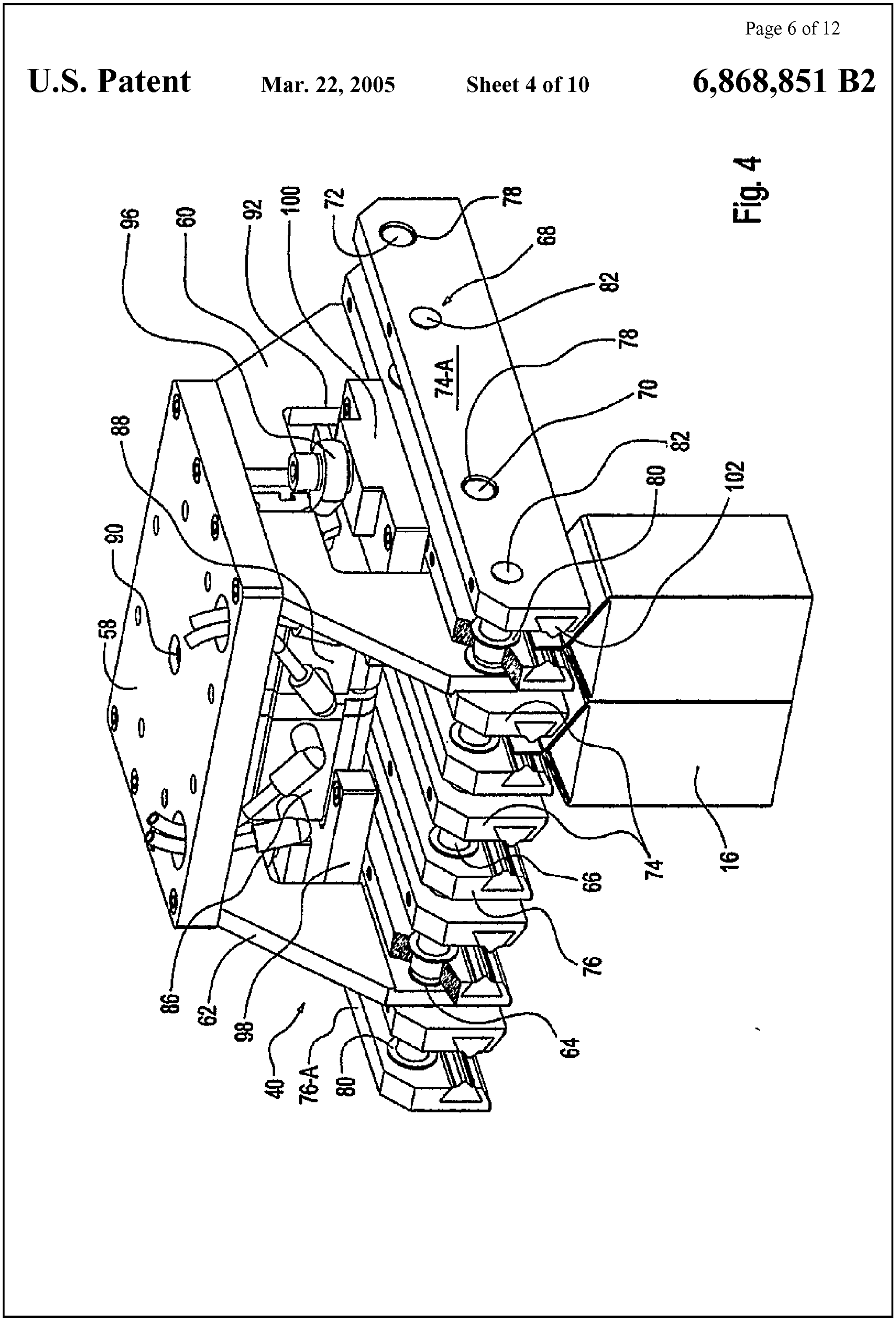
Figure 5:
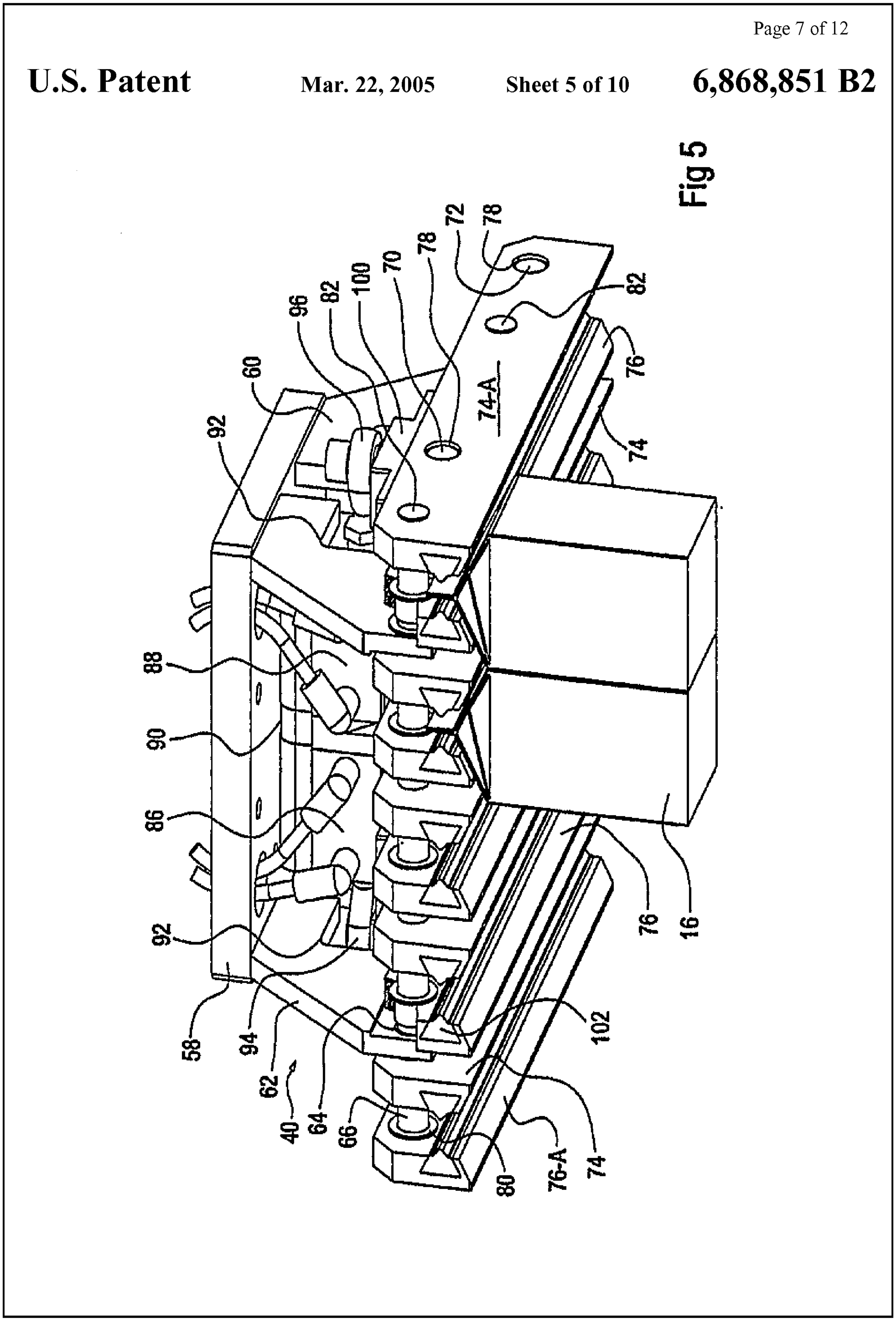
Figure 6:
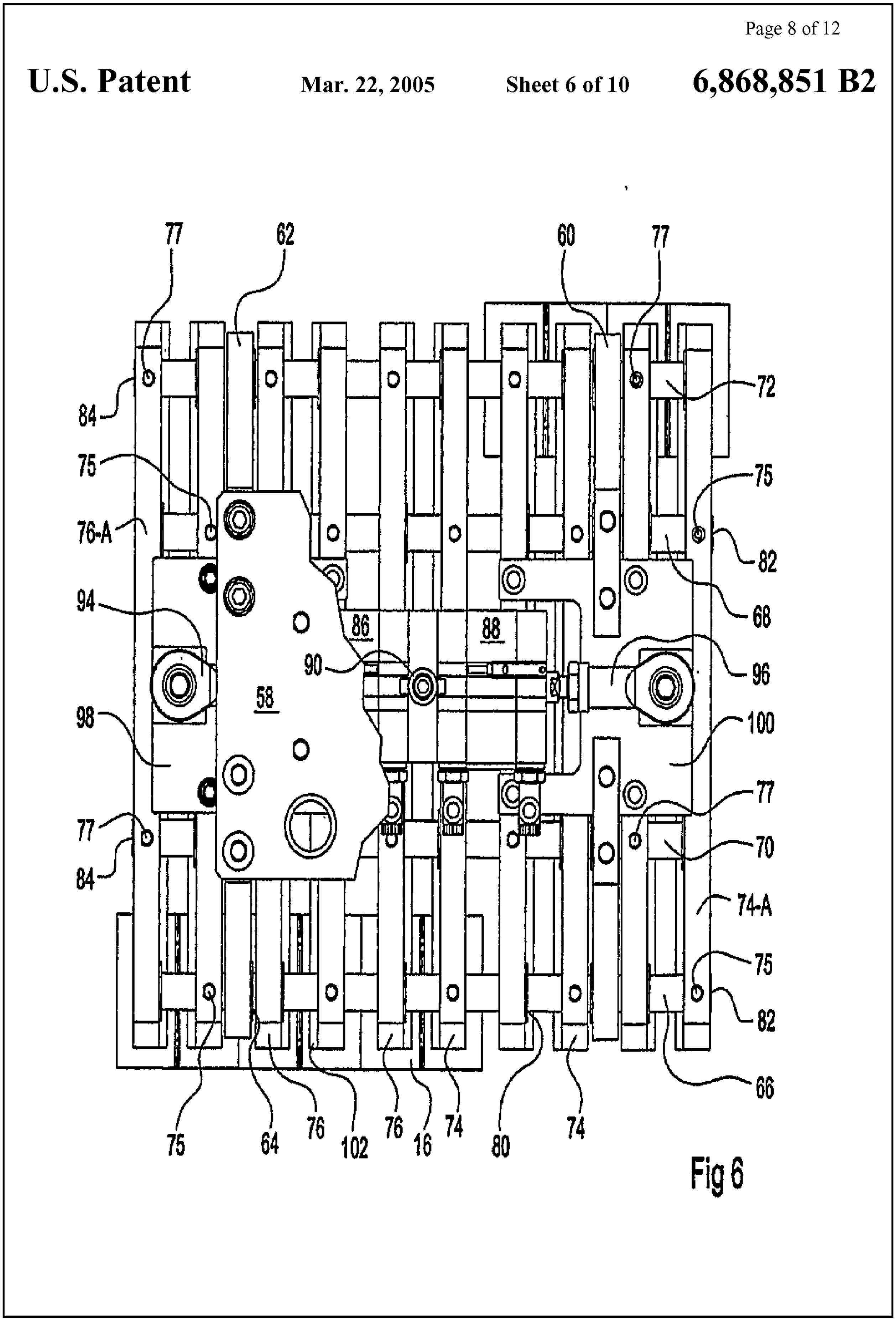
Figure 7:
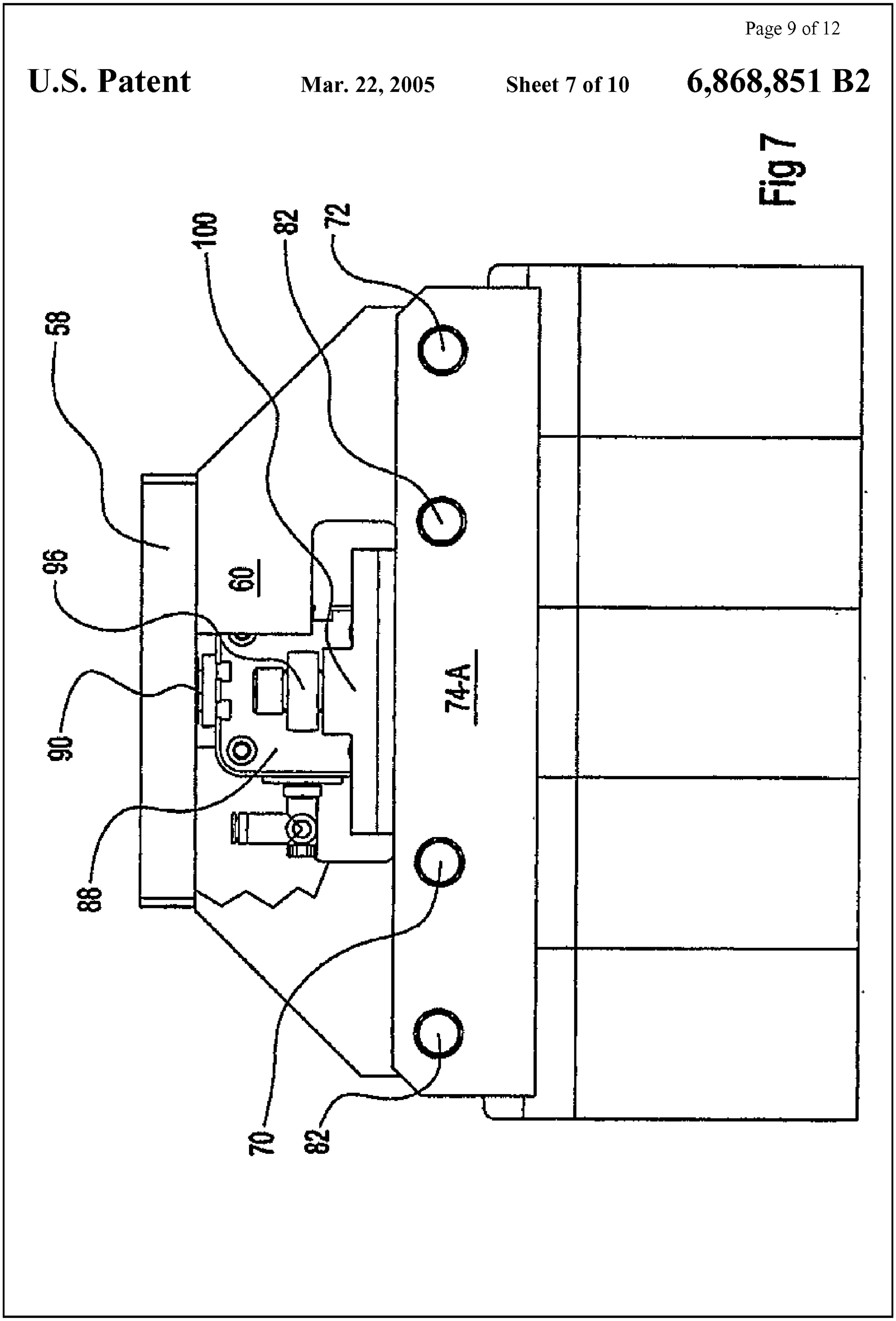
Figure 8:
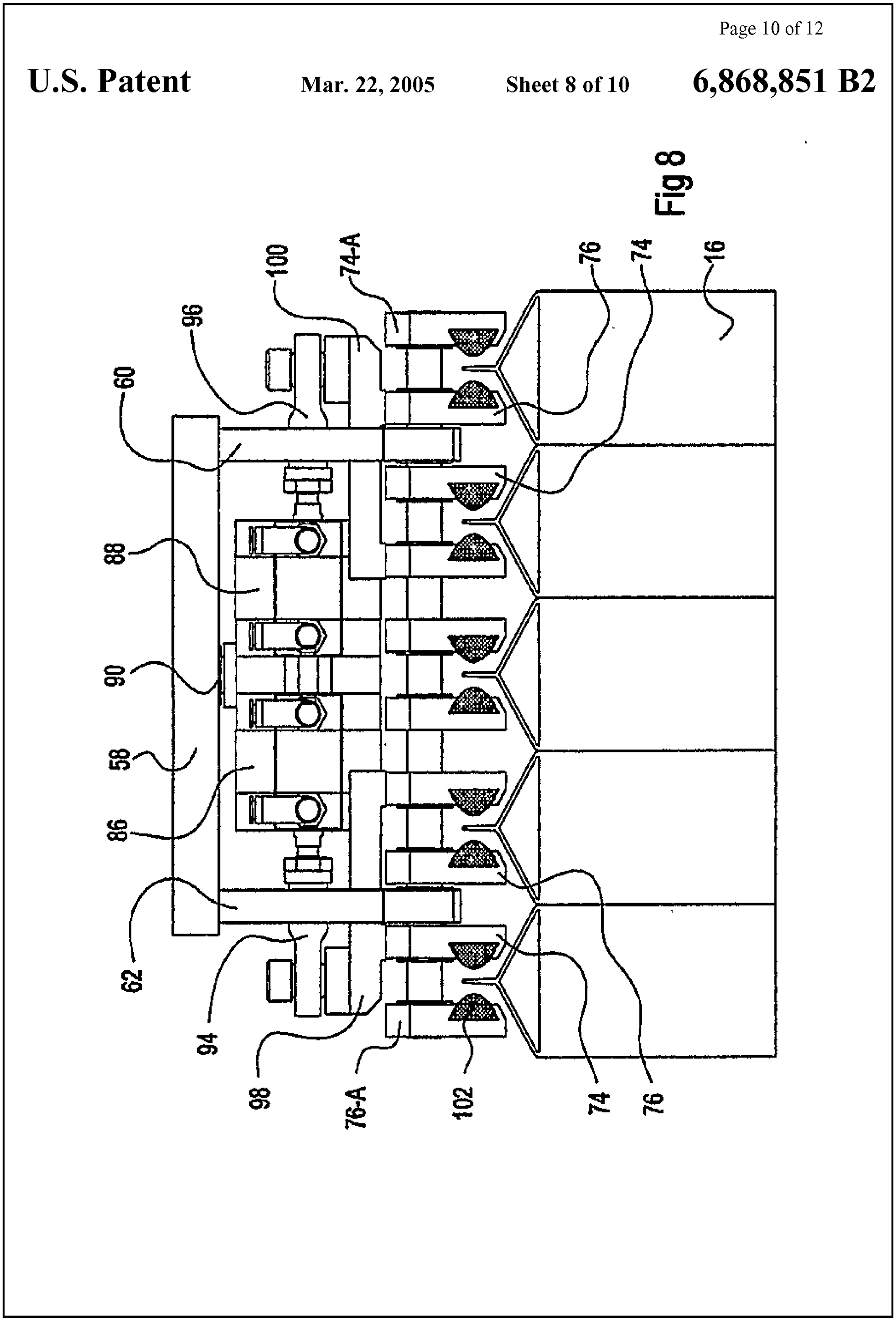
Figure 9:
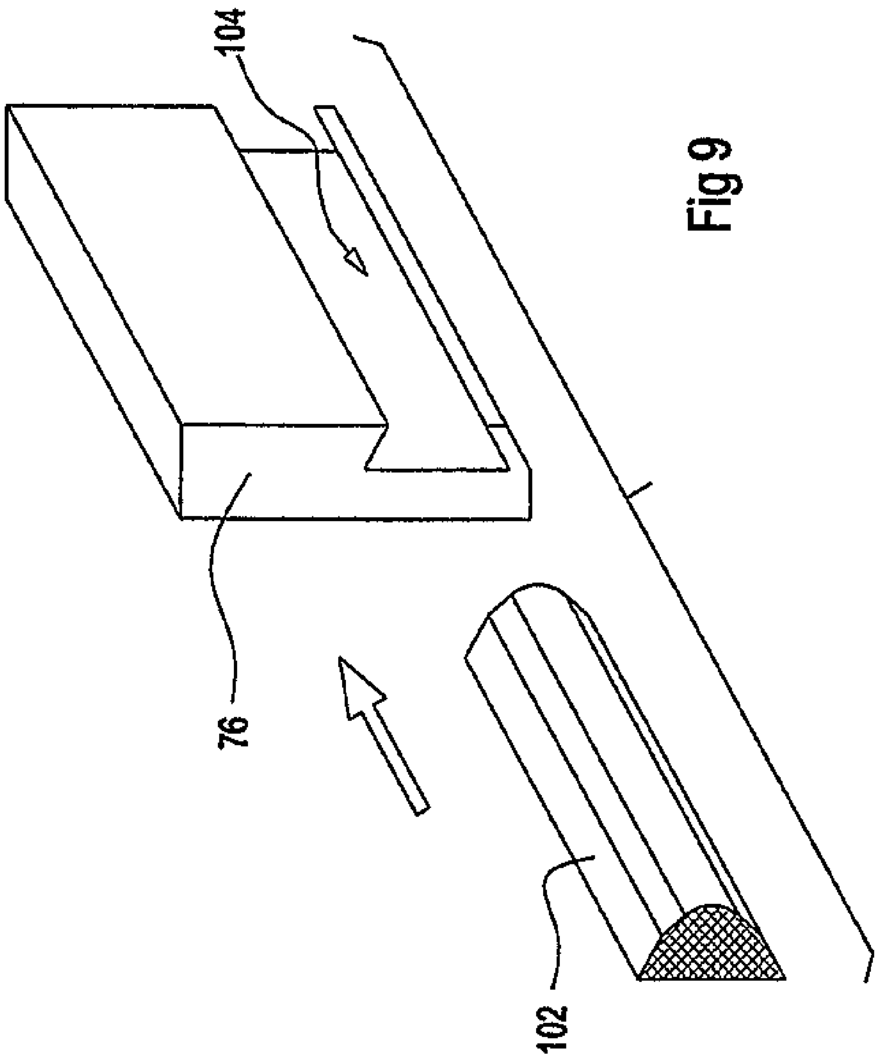
Figure 10:
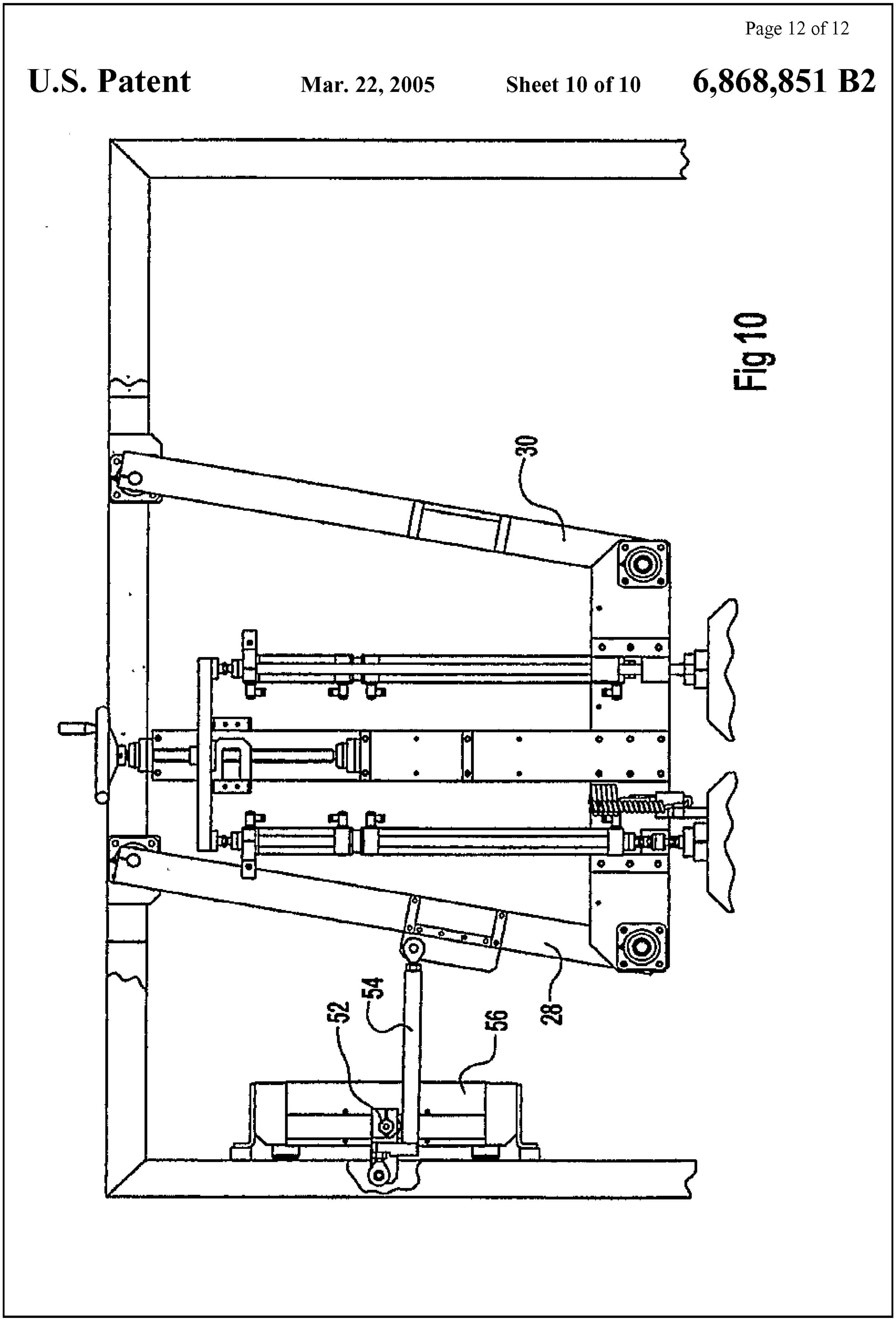

While in the foregoing description, liquid reservoir 60 is placed on plug member 44 after filling, it can also be placed on plug member 44 before filling, if desired. This could occur, for example, if it is necessary to refill chamber 82 to provide an additional dose of a drug to a patient Also, while the foregoing has described the filling means 78, 80 as mounted in one of the membranes 62, 64, it may also be located elsewhere on liquid reservoir 60, if desired. For example, it could be mounted on frame 66 as shown in FIG. 6.

It is recognized that other equivalents, alternatives, and modifications aside from those expressly stated, are possible and within the scope of the appended claims.

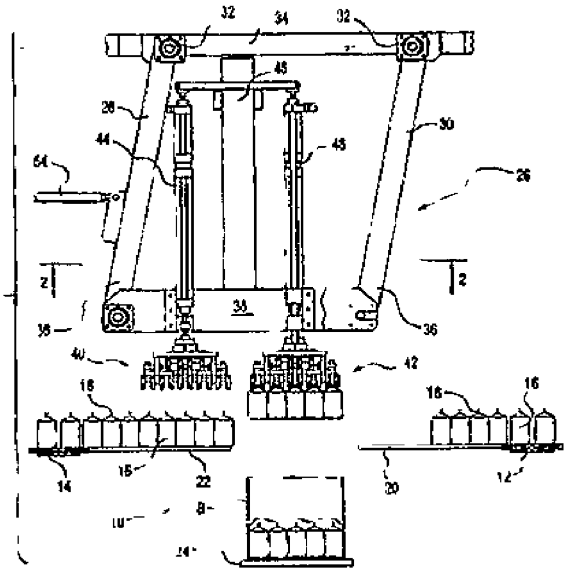

What is claimed is:

1. Liquid reservoir means for supplying liquid to a nebulizer for atomization, said liquid reservoir means comprising the combination of:

a liquid reservoir formed of first and second membranes positioned in a generally opposing relationship to form a closed chamber between the membranes for containing liquid, said first and second membranes being formed of a resilient material, said first and second membranes having opposing surfaces which are contiguous when the chamber is empty and spaced when said chamber is filled with liquid and thereby expanded, the expansion of the chamber distending said resilient material membranes to cause said resilient material membranes to apply pressure to liquid in the said chamber;

flow control means in communication with the chamber for controlling the discharge of liquid from the reservoir to the nebulizer under the pressure applied to the liquid by the distended resilient material membranes; and a member in the nebulizer having a surface on which one of said first and second membranes is contiguous and which receives said flow control means, said surface of said member being formed to deform at least one of said first and second membranes as a result of the contiguity of the membrane on the member to further increase the pressure on the liquid in said chamber.

2. Liquid reservoir means according to claim 1 wherein said surface of said member is formed to cause said membranes to progressively contact each other, commencing at a periphery of the membranes and extending toward a center of the membranes.

3. Liquid reservoir means according to claim 2 wherein said surface is formed so that a radius of curvature of said surface increases from a periphery of said surface to a center of said surface.

4. Liquid reservoir means according to claim 1 wherein said surface is formed to concavely deform at least one of said first and second membranes when viewed from the exterior of the chamber.

5. Liquid reservoir mans according to claim 1 wherein said flow control means is mounted in one of said first and second membranes.

6. Liquid reservoir means according to claim 5 wherein said surface concavely deforms said one of said first and second membranes.

7. Liquid reservoir means according to claim 1 further comprising means for retaining said liquid reservoir on the nebulizer.

8. Liquid reservoir means according to claim 7 wherein a filling means is mounted on said retaining means.

9. Liquid reservoir means according to claim 1 further including filling means in fluid communication with said chamber by which liquid may be supplied to said chamber.

10. Liquid reservoir means according to claim 9 wherein said filling means is mounted on a membrane.

11. Liquid reservoir means according to claim 9 wherein said filling means contains a valve.

12. Liquid reservoir means according to claim 9 wherein said filling means comprises means engagable with a syringe.

13. Liquid reservoir means according to claim 9 wherein said filling means comprises means mounted on a membrane for applying a force to the membrane for drawing the membranes apart to create an underpressure in the chamber formed between said membranes and means mounted on a membrane to admit liquid to said chamber responsive to said underpressure.

14. Liquid reservoir means of claim 13 wherein said means for drawing said membranes apart comprises a means engagable by a hand of a user to draw the membranes apart.

15. Liquid reservoir means of claim 14 wherein said means engageable by a hand of a user is removable.

16. Liquid reservoir means according to claim 13 wherein said means to admit liquid comprises said flow control means.

17. Liquid reservoir means of claim 16 wherein said flow control means has an end formed to engage a container for the liquid.

18. Liquid reservoir means according to claim 16 wherein said flow control means comprises a valve.

19. Liquid reservoir means of claim 18 wherein said valve has an inoperative state in which said valve operates as a check valve to prevent discharge of liquid from said chamber and an operative state for allowing the passage of liquid through the valve when said membranes are drawn apart.

20. Liquid reservoir means of claim 1 further defined as a liquid drug reservoir means.

* * * * *

UNITED STATES PATENT AND TRADEMARK OFFICE

CERTIFICATE OF CORRECTION

PATENT NO. : 6,868,851 B2
APPLICATION NO. : 10/062176
DATED : March 22, 2005
INVENTOR(S) : Heinonen It is certified that error appears in the above-identified patent and that said Letters Patent is hereby corrected as shown below:

Delete Title page illustrating figure, and substitute therefor, new Title page illustrating figure. (attached)

Delete drawing figures 1-10, and substitute therefor drawing figures 1-10, as shown on the attached sheets.

Signed and Sealed this

Second Day of January, 2007

JON W. DUDAS
*Director of the United States Patent and Trademark Office*

(12) United States Patent
Heinonen

(10) Patent No.: US 6,868,851 B2
(45) Date of Patent: Mar. 22, 2005

(54) LIQUID RESERVOIR FOR NEBULIZER

(75) Inventor: Erkki Heinonen, Helsinki (FI)

(73) Assignee: Instrumentarium Corp., Helsinki (FI)

(*) Notice: Subject to any disclaimer, the term of this patent is extended or adjusted under 35 U.S.C. 154(b) by 39 days.

(21) Appl. No.: 10/062,176

(22) Filed: Jan. 31, 2002

(65) Prior Publication Data

US 2003/0140919 A1 Jul. 31, 2003

(51) Int. Cl.[7] .................. A61M 11/00
(52) U.S. Cl. .................. 128/200.22; 128/203.12
(58) Field of Search .................. 128/203.12, 200.22, 128/200.21, 200.14; 222/321.1, 321.8, 383.1, 384; 239/321, 518, 524, 543, 544, 79-85, 102.2, 327, 330, 331, 338

(56) References Cited

U.S. PATENT DOCUMENTS

| | | | | | |
|---|---|---|---|---|---|
| 293,730 | A | * | 2/1884 | Goldman | 239/327 |
| 320,346 | A | * | 6/1885 | Goldman | 222/207 |
| 594,520 | A | * | 11/1897 | Bunnell et al. | 222/210 |
| 644,703 | A | * | 3/1900 | Buckley | 239/327 |
| 671,423 | A | * | 4/1901 | McTernen | 239/327 |
| 725,954 | A | * | 4/1903 | Goldman | 239/327 |
| 798,093 | A | * | 8/1905 | Dean | 604/204 |
| 1,754,382 | A | * | 4/1930 | Baracate | 228/53 |
| 2,578,864 | A | * | 12/1951 | Tupper | 222/215 |
| 2,625,432 | A | * | 1/1953 | Tupper | 239/327 |
| 2,760,209 | A | * | 8/1956 | Ewing et al. | 4/223 |
| 2,766,907 | A | * | 10/1956 | Wallace, Jr. | 222/94 |
| 2,870,574 | A | * | 1/1959 | Sheridan | 47/62 E |
| 3,089,624 | A | * | 5/1963 | Micallef | 222/386.5 |
| 3,259,321 | A | * | 7/1966 | Sellers | 239/310 |
| 3,404,843 | A | * | 10/1968 | Szekely | 239/338 |
| 3,848,808 | A | * | 11/1974 | Fetty et al. | 239/327 |
| 4,047,642 | A | * | 9/1977 | Nilson | 222/94 |
| 4,191,181 | A | * | 3/1980 | Franetzki et al. | 604/151 |
| 4,224,940 | A | | 9/1980 | Monnier | |
| 5,221,050 | A | * | 6/1993 | Jeffries et al. | 239/708 |
| 5,487,378 | A | * | 1/1996 | Robertson et al. | 128/200.16 |
| 5,497,944 | A | * | 3/1996 | Weston et al. | 239/321 |
| 5,515,842 | A | * | 5/1996 | Ramseyer et al. | 128/200.18 |
| 5,662,271 | A | * | 9/1997 | Weston et al. | 239/321 |
| 5,823,179 | A | * | 10/1998 | Grychowski et al. | 128/200.18 |
| 5,894,841 | A | | 4/1999 | Voges | |
| 5,957,891 | A | * | 9/1999 | Kriesel et al. | 604/132 |
| 6,029,660 | A | * | 2/2000 | Calluaud et al. | 128/203.12 |
| 6,056,213 | A | | 5/2000 | Ruta et al. | |
| 6,659,364 | B1 | * | 12/2003 | Humberstone et al. | 239/4 |

FOREIGN PATENT DOCUMENTS

| | | |
|---|---|---|
| EP | 1219313 | 7/2002 |
| EP | 1219314 | 7/2002 |
| WO | 01/19437 | 3/2001 |

* cited by examiner

*Primary Examiner*—Aaron J. Lewis
(74) *Attorney, Agent, or Firm*—Andrus, Sceales, Starke & Sawall, LLP

(57) ABSTRACT

A liquid reservoir for a nebulizer is comprised of a pair of membranes formed of resilient material and sealed about their edges to form a closed chamber between them for containing a liquid to be nebulized. When the chamber is filled with liquid and thereby expanded, the resilient membranes are distended to apply pressure to the liquid in the chamber. A discharge valve controls the discharge of liquid from the reservoir to the nebulizer under the pressure applied by the membranes. The reservoir is mounted on the nebulizer so that one of the membranes abuts a surface of the nebulizer that concavely deforms the membrane to increase the pressure applied to the liquid in the chamber to reduce or eliminate any residual volume of liquid in the chamber at the end of the discharging operation.

20 Claims, 4 Drawing Sheets